US008951202B2

(12) United States Patent
Borsook et al.

(10) Patent No.: US 8,951,202 B2
(45) Date of Patent: Feb. 10, 2015

(54) RECOGNIZING AWARENESS IN AN ANESTHETIZED SUBJECT

(76) Inventors: David Borsook, Concord, MA (US); Lino Becerra, Cambridge, MA (US); David Boas, Winchester, MA (US); Edward George, Belmont, MA (US)

( * ) Notice: Subject to any disclaimer, the term of this patent is extended or adjusted under 35 U.S.C. 154(b) by 974 days.

(21) Appl. No.: 12/658,897

(22) Filed: Feb. 16, 2010

(65) Prior Publication Data

US 2010/0217138 A1      Aug. 26, 2010

Related U.S. Application Data

(63) Continuation-in-part of application No. 11/722,145, filed as application No. PCT/US2005/047139 on Dec. 23, 2005, now abandoned.

(60) Provisional application No. 61/152,428, filed on Feb. 13, 2009, provisional application No. 61/222,441, filed on Jul. 1, 2009, provisional application No. 60/639,061, filed on Dec. 23, 2004.

(51) Int. Cl.
*A61B 5/02* (2006.01)
*A61B 5/026* (2006.01)
*A61B 5/1455* (2006.01)
*A61B 5/00* (2006.01)

(52) U.S. Cl.
CPC ............ *A61B 5/0261* (2013.01); *A61B 5/14553* (2013.01); *A61B 5/4821* (2013.01); *A61B 2562/0233* (2013.01); *A61B 2562/046* (2013.01)
USPC ............................. 600/483; 600/504; 600/340

(58) Field of Classification Search
CPC ............ A61B 5/0261; A61B 5/14553; A61B 5/4821; A61B 5/0265; G06K 9/00
USPC .................. 600/504–507, 323–342, 410, 419, 600/454–463
See application file for complete search history.

(56) References Cited

U.S. PATENT DOCUMENTS

| 5,198,977 | A  | * | 3/1993  | Salb ............................ 382/128 |
| 6,240,309 | B1 | * | 5/2001  | Yamashita et al. ............ 600/407 |
| 2004/0064052 | A1 | * | 4/2004  | Chance et al. ................ 600/476 |
| 2004/0082862 | A1 | * | 4/2004  | Chance ......................... 600/473 |
| 2005/0228291 | A1 | * | 10/2005 | Chance ......................... 600/476 |
| 2006/0116556 | A1 | * | 6/2006  | Duhamel ...................... 600/300 |

* cited by examiner

*Primary Examiner* — Navin Natnithithadha
*Assistant Examiner* — Eric Messersmith
(74) *Attorney, Agent, or Firm* — Quarles & Brady, LLP (57) ABSTRACT

A method for recognizing awareness in a subject includes performing optical imaging on at least one cortical region of the brain of the subject. Optical imaging data are obtained over time measuring one or more hemodynamic parameters in the at least one cortical region of the subject's brain. An observed variation pattern is determined in the measured hemodynamic parameters, and the observed variation pattern is compared to one or more known variation patterns characteristic of awareness. Substantial similarity between the observed and known variation patterns signals awareness in the subject.

19 Claims, 8 Drawing Sheets

RECOGNIZING AWARENESS IN AN ANESTHETIZED SUBJECT

CROSS-REFERENCE TO RELATED APPLICATIONS

This application is based on and claims the benefit of U.S. Provisional Patent Application No. 61/152,428, filed Feb. 13, 2009, and U.S. Provisional Patent Application No. 61/222, 441, filed Jul. 1, 2009; this application is also a continuation-in-part of U.S. patent application Ser. No. 11/722,145, filed on Jun. 19, 2007, which is a U.S. National Phase Application of PCT Application No. PCT/US2005/047139, filed on Dec. 23, 2005, which claims the benefit of U.S. Provisional Patent Application No. 60/639,061, filed on Dec. 23, 2004; and all of the aforementioned priority documents are hereby incorporated by reference in their entirety.

STATEMENT OF FEDERALLY SPONSORED RESEARCH OR DEVELOPMENT

Not applicable.

BACKGROUND OF THE INVENTION

The present invention is directed to systems and methods for monitoring patients during medical procedures and, more particularly, to systems and methods for determining when a patient is cognitively experiencing particular sensations.

Many types of medical procedures involve the use of anesthetics, analgesics, and other sedation or partial sedation methods. For example, general anesthetics are administered before some procedures to suppress pain throughout the patient's entire body. General anesthetics also render the subject unconscious and amnesiac during the procedure. These effects not only reduce stress on the subject, but also simplify the procedure for practitioners if the anesthetics are administered with immobilizing drugs (i.e., muscle blockers). That is, subconscious patient movements are prevented and therefore cannot interfere with actions of the practitioners and complicate the procedure.

Unfortunately, it can be difficult to precisely dose anesthetics or other drugs designed to sedate or render the patient amnesiac to achieve the desired effects because dose is determined by many factors including the subject's age, medical history, current medications, previous use of anesthetics, current condition (e.g., unstable or critical), and the like. Furthermore, some factors exacerbate the effect of others, and in some situations (e.g., if the subject is unstable) the subject's condition may completely obscure the effects of other factors. As such, for example, anesthesiology is largely based on heuristics and an anesthesiologist's experience.

The complexity of anesthesiology and other such undertakings sometimes results in insufficient dosing before medical procedures. In a small number of cases, this ultimately leads to unintended subject awareness (i.e., consciousness) or subconscious sensations of pain during the procedure. In the former case, the subject may not be able to communicate with medical practitioners if an immobilizing drug has also been administered. In these situations, the subject typically experiences panic and even lasting psychological problems after the procedure, such as post traumatic stress disorder.

Furthermore, the problems described above may also complicate procedures that involve regional anesthetics (i.e., anesthetics that only render part of the subject's body insensitive to pain). In these procedures, the subject remains conscious and, in some cases, may even need to move in a manner that assists in maneuvering medical equipment within the body. Nevertheless, the subject is typically heavily sedated in such procedures to reduce stress. As such, the subject may be incapable of communicating with practitioners regarding potential pain sensations and the ineffectiveness of anesthetics.

Complex methods of determining awareness of non-communicative subjects have been developed to address the problems described above. For example, functional MR images may show subject brain activity associated with awareness. However, conducting MR imaging during many types of medical procedures is impractical due to equipment unavailability, relatively large physical sizes, and relatively high operating costs among other reasons.

Therefore, it would be desirable to have an efficient, relatively inexpensive, and substantially objective method for recognizing subject consciousness and sensation of pain during medical procedures.

SUMMARY OF THE INVENTION

In a first aspect, the present invention provides a method for recognizing awareness in a subject. The method comprises performing optical imaging using a optical imaging system on at least one cortical region of the brain of the subject. Optical imaging data are obtained over time measuring one or more hemodynamic parameters in the at least one cortical region of the subject's brain. An observed variation pattern is determined in the measured hemodynamic parameters, and the observed variation pattern is compared to one or more known variation patterns characteristic of awareness. Substantial similarity between the observed and known variation patterns signals awareness in the subject.

In some embodiments, the hemodynamic parameter is blood flow. Furthermore, in some embodiments, blood flow is measured by detecting optical signals from oxygenated hemoglobin.

In some embodiments, the at least one cortical region of the brain is selected from the somatosensory cortex, the supplementary motor cortex, and the frontal cortex.

In some embodiments, the method additionally comprises the step of performing an activity on the subject that would inflict pain on the subject if the subject were aware. In some embodiments, the known variation pattern indicating awareness comprises two sequential peaks in blood flow over time, and two sequential peaks signal a sensation of pain in the subject.

In some embodiments, the optical imaging is bilaterally performed on the somatosensory cortex, and the known variation pattern indicating awareness bilaterally comprises two sequential peaks in blood flow over time.

In some embodiments, the known variation pattern indicating awareness has a substantial time delay between performing the pain-inducing activity and the occurrence of a peak in blood flow, and the time delay signals a sensation of pain in the subject. Furthermore, in some embodiments, the substantial time delay is greater than about ten seconds.

In some embodiments, the method additionally comprises the step of applying an innocuous test stimulus to the subject.

In some embodiments, the optical imaging is bilaterally performed on the somatosensory cortex, and the known variation pattern indicating awareness contains both ipsilateral and contralateral optical imaging data. In some embodiments, the known variation pattern indicating awareness comprises a substantially reduced peak of blood flow with respect to time in the ipsilateral somatosensory cortex as compared to the contralateral somatosensory cortex, and the reduced peak signals a sensation of innocuous touch in the subject. Furthermore, in some embodiments, known variation pattern shows peak blood flow with respect to time in the ipsilateral somatosensory cortex is approximately 55% of the peak blood flow with respect to time in the contralateral somatosensory cortex.

In some embodiments, the one or more known variation patterns characteristic of awareness is obtained from control data for the hemodynamic parameter. In some embodiments, the control data is obtained by the additional step of performing optical imaging on the at least one cortical region of the subject's brain when the subject is conscious. In some embodiments, the method further comprises the step of administering an anesthetic to the subject after obtaining the control data. In some embodiments, the step of obtaining the control data includes performing optical imaging on the supplementary motor cortex of the subject's brain when the subject is either moving or consciously imagining movement.

In some embodiments, the at least one cortical region of the subject's brain is the supplementary motor cortex and the one or more known variation patterns characteristic of awareness is the blood flow pattern in the supplementary motor cortex characteristic of consciously imagined movement. In some embodiments, the blood flow pattern characteristic of consciously imagined movement comprises a rounded peak of maximum blood flow.

In another aspect, the present invention provides a method for evaluating a treatment comprising administering the treatment to a subject. A Noxious stimulus is applied to the subject while using an optical imaging system to perform optical imaging on the subject and thereby obtain brain activity data representing a hemodynamic parameter in at least one cortical region of the subject's brain. The brain activity data representing the hemodynamic parameter in the at least one cortical region of the subject's brain are compared to control data representing the hemodynamic parameter.

In some embodiments, the method further comprises using the optical imaging system to perform optical imaging on the subject and thereby obtain the control data before obtaining the activity data. In some embodiments, a reduction in intensity of the hemodynamic parameter from the control data to the brain activity data indicates the treatment is a pain-relieving treatment. Furthermore, in some embodiments, the reduction in intensity of the hemodynamic parameter from the control data to the brain activity data indicates the efficacy of the pain-relieving treatment.

Other aspects of the invention will be apparent from the following description and the claims.

BRIEF DESCRIPTION OF THE DRAWINGS

The invention will hereafter be described with reference to the accompanying drawings, wherein like reference numerals denote like elements, and.

DETAILED DESCRIPTION OF THE INVENTION

The present invention generally provides methods for recognizing unintended awareness in an anesthetized subject. As described herein, "awareness" is indicated by brain activity that correlates with conscious or subconscious planned movement and/or the sensation of pain, although other indicators may be considered as well. In any case, the methods of the present invention are based on imaging techniques that are relatively simple and inexpensive compared to other imaging techniques, such as CT and MRI. Furthermore, the present invention also provides methods other than those for recognizing unintended awareness in an anesthetized subject. For example, because the techniques described herein can be used to objectively measure subject pain, the present invention also provides improved methods for identifying analgesic compounds and determining their efficacy. In the following paragraphs, a system for performing methods of the present invention is first described, followed by various methods that can be performed according to the present invention.

Figure 1:
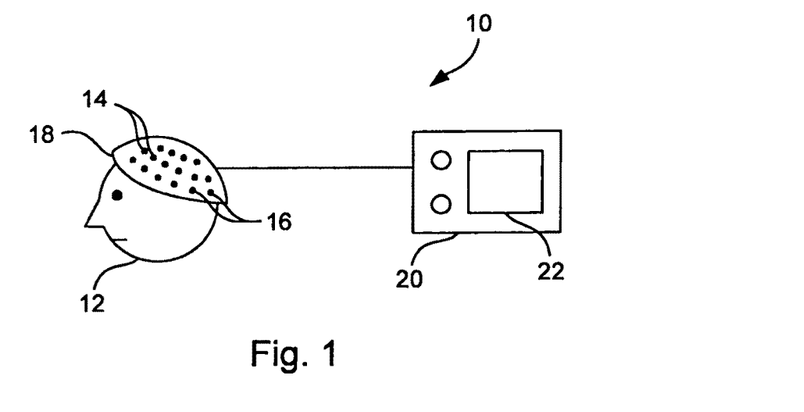
FIG. 1 is a schematic diagram of an optical imaging system used with the present invention.
Figure 2:
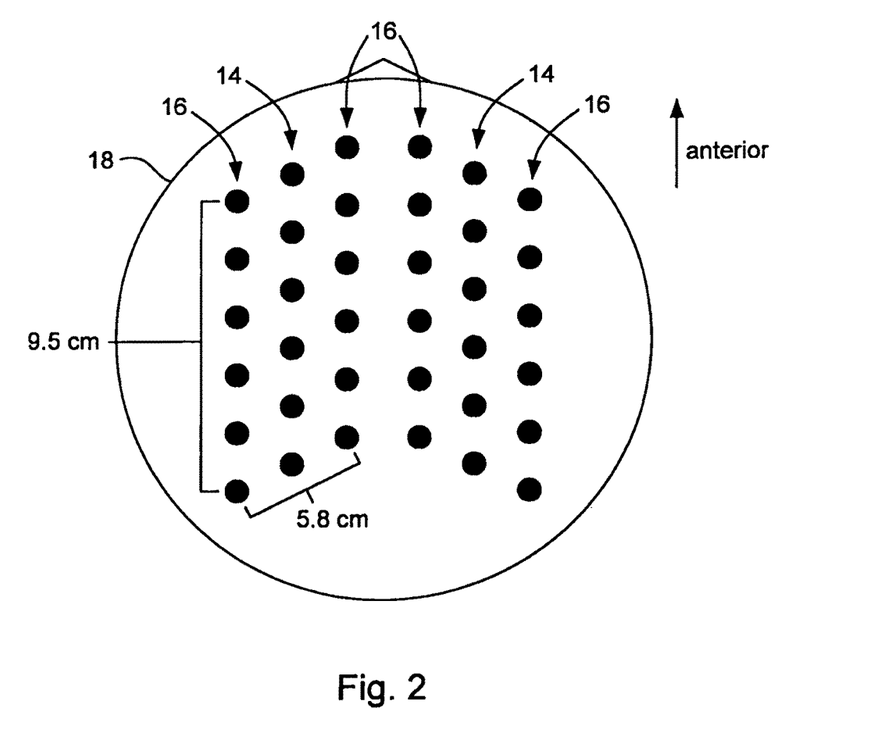
FIG. 2 is a schematic diagram of an array of light sources and detectors on a head cap of the imaging system.

Referring to FIGS. 1 and 2, the present invention uses an optical imaging system 10. The optical imaging system 10 may be a diffuse optical imaging (DOI) system, such as a near infrared spectroscopy (NIRS) system manufactured by TechEn, Inc. of Milford, Mass., to noninvasively provide images of the brain of a subject 12. In general, the system 10 emits light from one or more sources 14 into the subject 12 and then uses one or more detectors 16 to detect the light scattered from tissues and chemicals in the subject's brain. In the present invention, the light sources 14 and detectors 16 are supported on a head cap 18 and may be arranged as shown in FIG. 2, although other configurations are also possible. For example, the sources 14 and detectors 16 may be arranged in a different configuration if the medical procedure includes operating on the subject's scalp or brain. Furthermore, fewer sources 14 and detectors 16 may be used to obtain data from only a specific area of the subject's brain (e.g., the somatosensory cortex).

Regardless of the configuration of the sources 14 and detectors 16, the detectors 16 dynamically detect light scattered by oxy-hemoglobin and deoxy-hemoglobin within the subject's brain. As described in further detail below, these chemicals are observed to determine blood flow rates within the brain, which correlate with planned movement and sensations of pain. The detectors 16 transmit data regarding hemodynamics, and therefore planned movement and sensations of pain, to a processor 20. The processor 20 removes noise from the data in a standard manner and, in some embodiments, models data as a standard function, such as a gamma function. The processor 20 may also model data from each detector 16 separately and display the data on a monitor 22 on separate or combined graphs (e.g., see FIGS. 3 and 4).

Contrast agents other than hemoglobin may be used in the system 10 without departing from the scope of the invention. In some embodiments, a dye (i.e., a compound capable of absorbing the source wavelength of light) is introduced into the blood of the subject 12. Exemplary contrast agents are non-toxic and include rifampin (red), β-carotene (orange), tetracycline (yellow), indocyanine green, Evan's blue, methylene blue; soluble inorganic salts such as copper sulfate (green or blue), $Cu(NH_3)_4\ 2+$ (dark blue), permanganate (purple), $NiCl_2$ (green), $CrO_4\ 2-$ (yellow), $Cr_2O_7\ 2-$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40, FD&C Yellow No. 5 (Tartrazine), FD&C Yellow No. 6 (Sunset Yellow FCF), and the like.

The dispersible chromophores listed above are generally 1) water-soluble at physiological pH, although fat-soluble chromophores (such as (3-carotene) will are also effective if they are rapidly flushed from tissue, or 2) digestible or metabolizable through enzymatic pathways (such as methylene blue, which is rapidly metabolized by mitochondrial reductases, and proteins which are digested by proteases). In some cases, it may be possible to modify a chromophore to improve its dispersibility. A particular advantage of protein chromophores is that they can be conjugated to degradation inducing moieties, such as degradation signaling polypeptides using standard biochemical techniques. For example, green fluorescent protein can be conjugated to ubiquitin, which facilitates breakdown of the protein into small, invisible peptides by the eukaryotic ubiquitin proteolysis pathway.

Other considerations for DOI systems and parameters for observation of a subject's brain are further described in U.S. Pat. Nos. 6,516,214 and 6,577,884, the disclosures of which are hereby incorporated by reference.

From the previous paragraphs, it should be apparent that the system 10 is relatively simple compared to other imaging systems. Furthermore, the low cost, relatively compact size, and capability to obtain continuous, real-time information on cerebral hemodynamics provide advantages over other techniques such as CT and MRI.

The system 10 is used during a medical procedure to monitor specific areas of subject's brain (i.e., the frontal cortex and the somatosensory cortex) for specific changes in blood flow (i.e., changes in blood flow rate over a given time period). Some changes in blood flow have been found to indicate motion planning and/or sensations of pain experienced by the subject 12. Conversely, other changes in blood flow have been found to indicate that the subject 12 feels sensations of innocuous touch.

In order to determine if blood flow changes indicate motion planning and/or sensations of pain, the brain activity data obtained from the system 10 may be evaluated in several manners. For example, the brain activity data may be modeled and reviewed (manually or via the processor 20) for specific variation patterns that correlate with awareness. As another example, the brain activity data may be compared to reference or control data obtained before the medical procedure begins. These alternatives for brain activity data evaluation are described in further detail in the following paragraphs.

As described above, the brain activity data may be evaluated for DOI dataforms that the inventors of the present invention have found to correlate with certain sensations of touch. In some embodiments, the processor 20 may provide information to the monitor 22 (FIG. 1) such that the brain activity data are continuously displayed during a procedure. A medical practitioner may then continuously evaluate the activity data during the procedure to determine if the subject is conscious or subconsciously experiencing pain. In other embodiments, the processor 20 may be programmed to continuously monitor the brain activity data for specific variation patterns. Methods for programming the processor 20 to automatically monitor the activity data for specific patterns will be recognized by those skilled in the art and may be used without departing from the scope of the invention.

Figure 3:
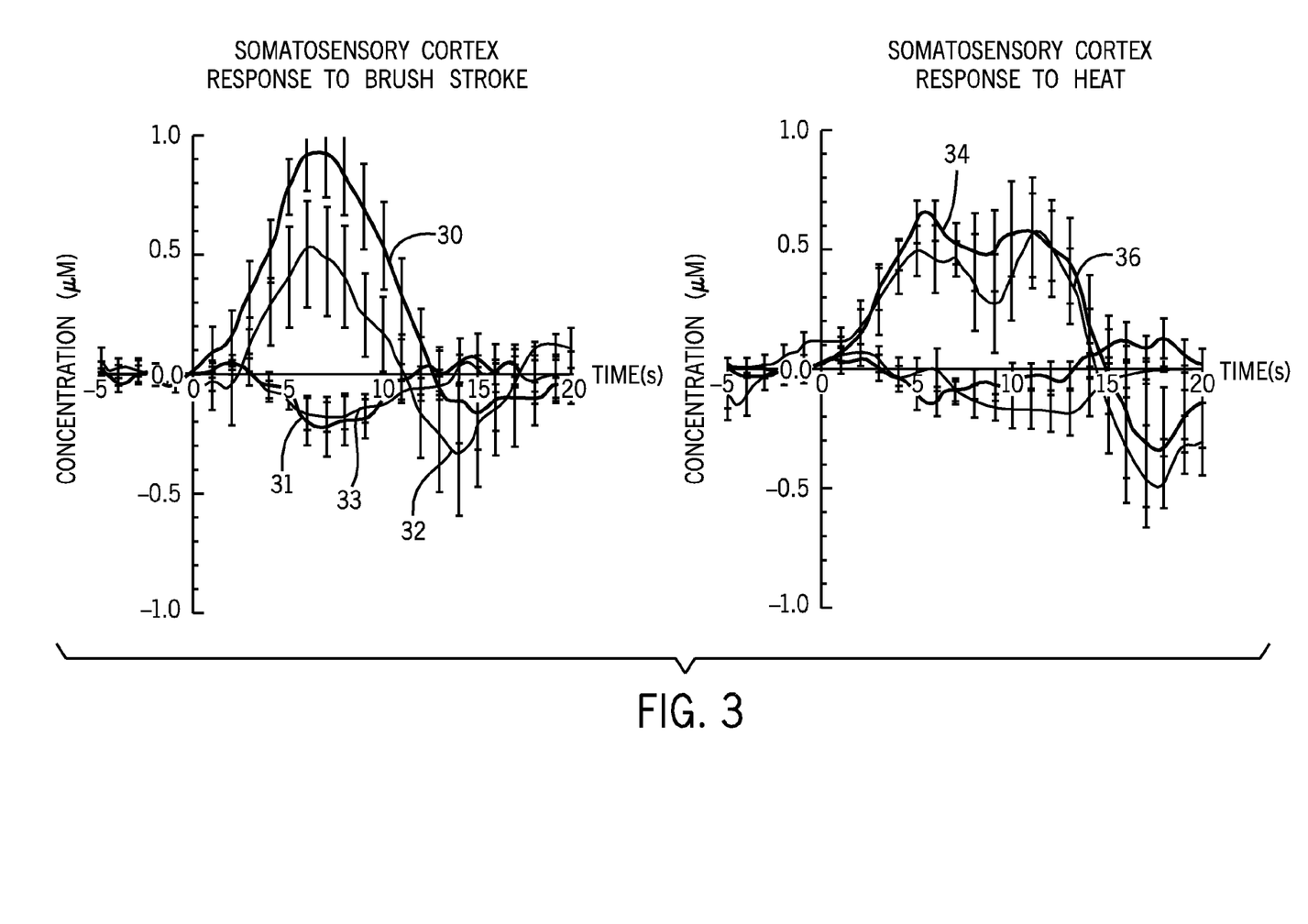
FIG. 3 shows average somatosensory cortex hemodynamic responses to a brush stroke when applied to a group of subjects (left panel) and average somatosensory cortex hemodynamic responses to heat when applied to the group of subjects (right panel) as measured by diffuse optical imaging (DOI)
Figure 4:
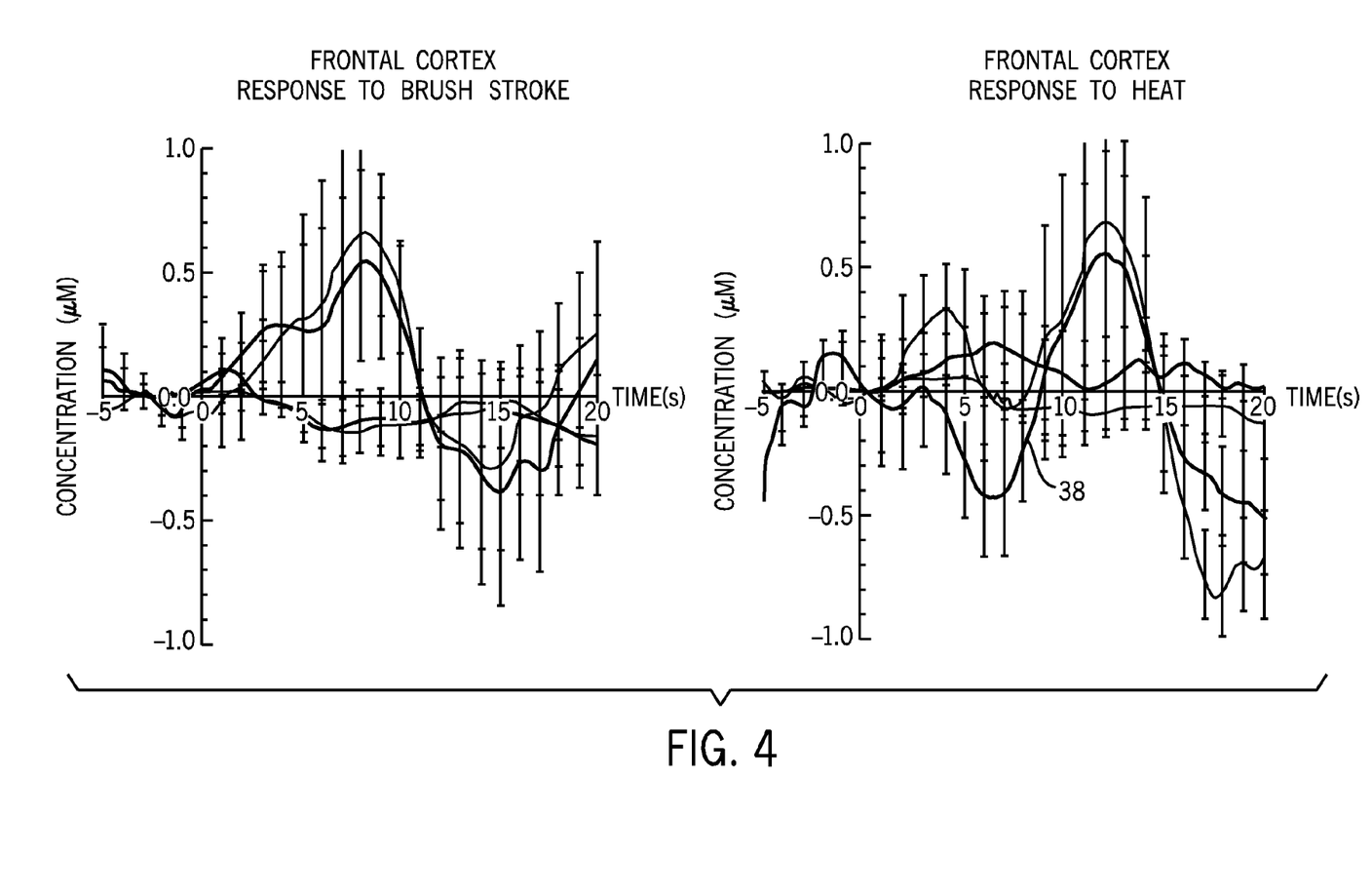
FIG. 4 shows average frontal cortex hemodynamic responses to a brush stroke when applied to a group of subjects (left panel) and average frontal cortex hemodynamic response to heat when applied to the group of subjects (right panel) as measured by DOI.
Figure 5:
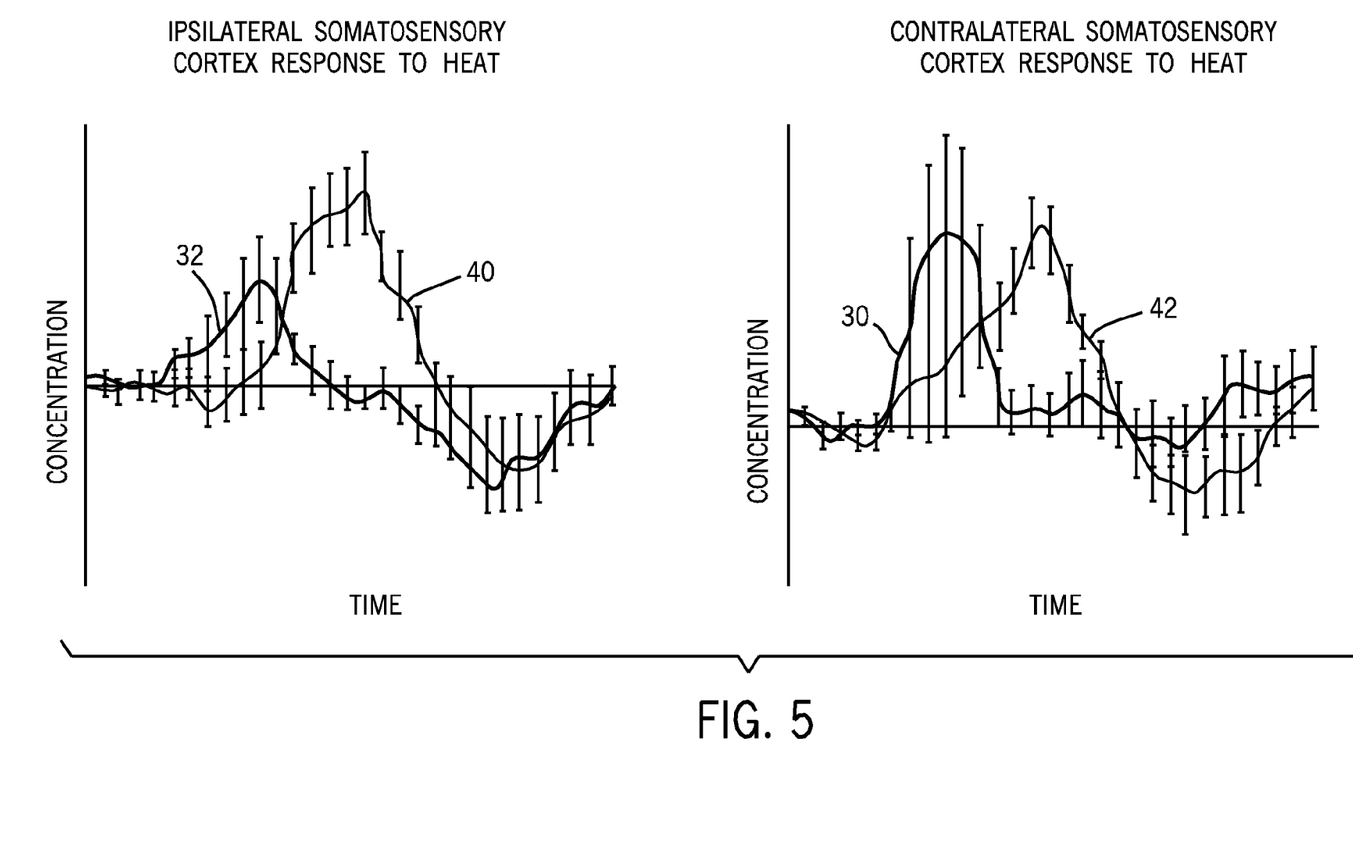
FIG. 5 shows average somatosensory cortex hemodynamic responses to both low heat and high heat when applied to a group of subjects as measured by DOI.
Figure 6:
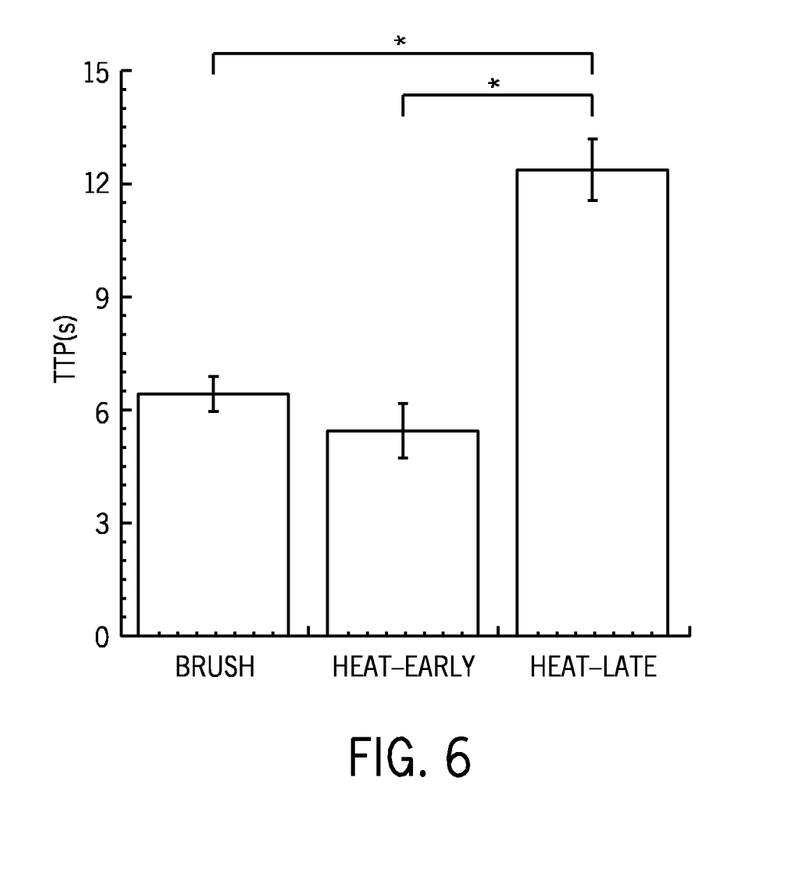
FIG. 6 shows time to peak results for brush and heat stimuli applied to a group of subjects as measured by DOI.

Regardless of the how the brain activity data is monitored, the observed data patterns may be reviewed for known variation patterns such as those shown in FIGS. 3-5. As a first example, the brain activity data may be evaluated for a greater contralateral somatosensory cortex peak response 30 than the ipsilateral peak response 32 (e.g., the ipsilateral response 32 being 55%±10% of the contralateral response 30) as shown in FIGS. 3 and 5. Such a pattern has been correlated with an innocuous brush stroke stimulus and a low-pain heat stimulus (i.e., 43° C. thermode). As a second example, the brain activity data may be evaluated for a "double peak" somatosensory cortex response (i.e., higher intensity data followed by lower intensity data then followed by higher intensity data), such as the bilateral contralateral response 34 and ipsilateral response 36 shown in FIG. 3. Furthermore, the brain activity data may be monitored for a time delay from a stimulus to the second peak as shown in FIG. 6. Such a time delay is greater than about ten seconds and is more specifically about 12.5 seconds. These patterns have been correlated with a 46° C. noxious heat stimulus. As a third example, the activity data may be evaluated for an intense negative frontal cortex response followed by an intense positive frontal cortex response, such as the contralateral response 38 shown in FIG. 4. This pattern has also been correlated with a 46° C. noxious heat stimulus. As a fourth example, the activity data may be evaluated for a "single peak" ipsilateral somatosensory cortex response 40 that is approximately equal to the contralateral response 42 in intensity (±10%). Such a pattern has been correlated with a high-pain heat stimulus (i.e., 49° C. thermode).

Figure 7:
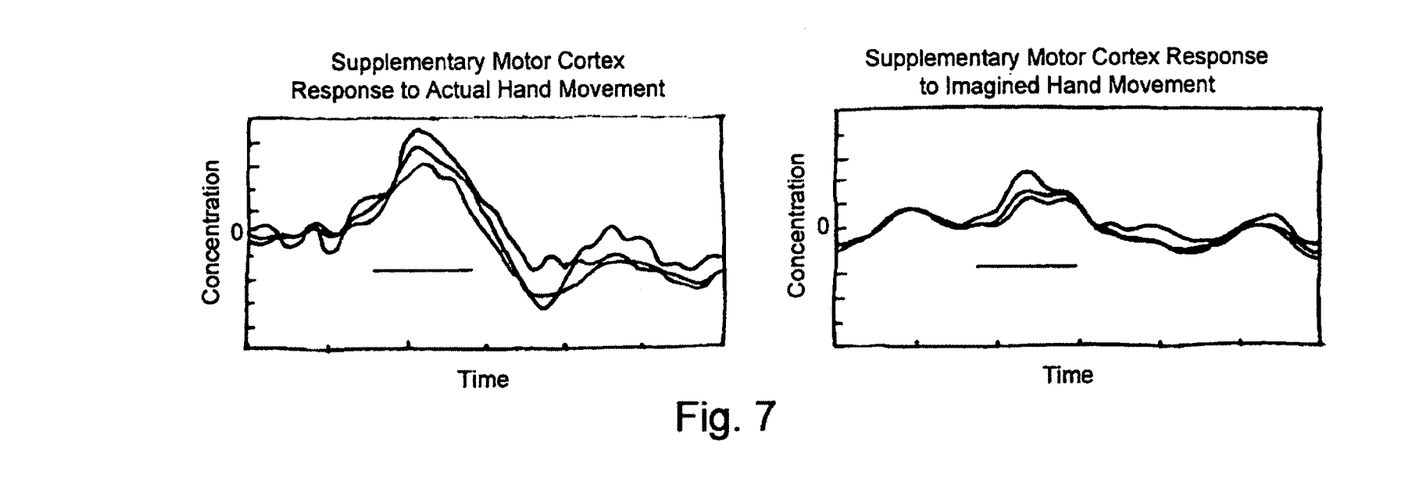
FIG. 7 shows supplementary motor cortex hemodynamic response to actual hand movement by a subject (left panel) and supplementary motor cortex hemodynamic response to imagined hand movement by the subject (right panel)

As briefly described above, the brain activity data obtained during a medical procedure may also be evaluated by comparison to control data that are not necessarily similar to the responses described in the previous paragraph. Such control data may be obtained in various manners. For example, the control data may be obtained by the system 10 from the subject of the medical procedure prior to administering anesthetics. To obtain the control data, the subject may be asked to perform actions or subjected to actions to obtain correlations with specific blood flow changes within the subject's brain. For example, the subject may be asked to perform or imagine performing various physical activities, such as sitting up from a lying-down position, moving their arms and legs, walking, running and the like, so that motion control data (i.e., control data indicating motion) and motion planning control data (i.e., control data indicating motion planning) may be obtained. Exemplary motion and motion planning control data obtained from the supplementary motor cortex of an actual subject are shown in FIG. 7.

As an alternative or in addition to the previous manner of obtaining control data, the subject may be subjected to various touch stimuli. That is, one or more innocuous stimuli (e.g., brush stroke via a soft toothbrush) may be applied so that innocuous control data (i.e., control data indicating a sensation of innocuous touch) may be obtained. Exemplary innocuous control data obtained from an actual group of subjects are shown in FIGS. 3 and 4. Materials and methods for obtaining these data are further described in the example below. As an alternative or in addition to obtaining innocuous control data, the subject may be subjected to one or more noxious stimuli (e.g., a thermode having a temperature of about 46° C.) so that noxious control data (i.e., control data indicating a sensation of pain) may be obtained. Exemplary noxious control data obtained from an actual group of subjects are shown in FIGS. 3 and 4.

Furthermore, control data for various levels of pain may also be obtained. That is, one or more low-pain stimuli (e.g., a thermode that provides a pain rating of 3 out of 10; about 43° C.) may be applied so that low-pain noxious control data (i.e., control data indicating a mild sensation of pain) may be obtained. Exemplary low-pain noxious control data obtained from an actual group of subjects are shown in FIG. 5 at reference numbers 30 and 32. The subject may also be subjected to one or more high-pain noxious stimuli (e.g., a thermode that provides a pain rating of 7 out of 10; about 49° C.) so that high-pain noxious control data (i.e., control data indicating an intense sensation of pain) may be obtained. Exemplary high-pain noxious control data obtained from an actual group of subjects are shown in FIG. 5 at reference numbers 40 and 42. Of course, normal control data (i.e., control data obtained when the subject is not performing or imagining performing physical activities and no stimuli are applied to the subject) may also be obtained.

The aforementioned stimuli may be applied to the subject at the anatomic location of the medical procedure to obtain data showing specific distinctions between brain responses corresponding to innocuous and noxious sensations at the anatomic location. Alternatively, the stimuli may be applied to various anatomic locations to obtain data showing general distinctions between brain responses corresponding to innocuous and noxious sensations.

As an alternative to obtaining control data from a single subject, the manners of obtaining control data described above may be used with an aggregate of subjects. Similarly, control data may be obtained from a database (e.g., an electronic server) having control data from procedures performed in various medical facilities. In either case, brain activity data from the system 10 may be compared to control data from a large group of subjects, control data only from similar subjects (i.e., subjects having a similar age and medical history), or the like.

Regardless of how the control data are obtained, they may be compared to the brain activity data from the system 10 in various manners. In the simplest form, the processor 20 may provide information to the monitor 22 (FIG. 1) such that both the control data and the activity data are displayed during a procedure. A medical practitioner may then continuously compare the control data and activity data during the procedure to determine if the subject is aware.

Figure 8:
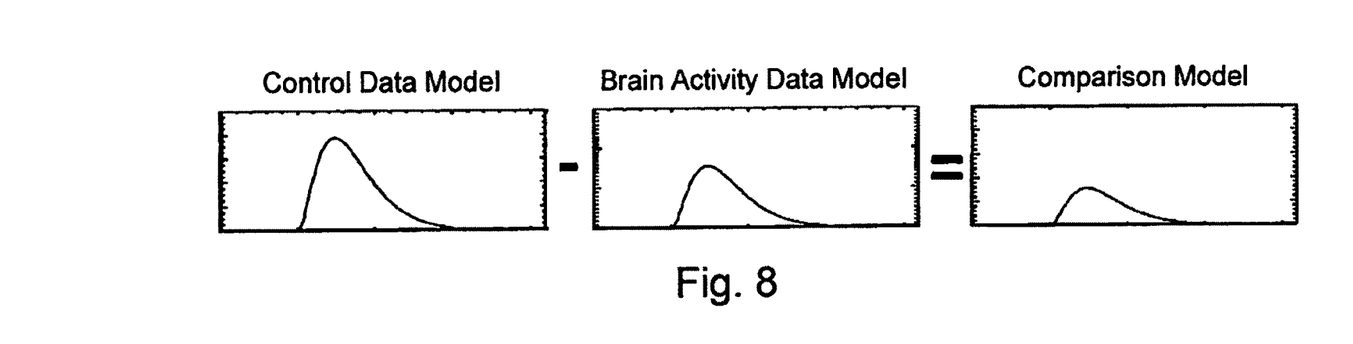
FIG. 8 shows an exemplary comparison model that could be used to determine awareness derived by comparing a control data model to a brain activity data model.

As another alternative, the processor 20 may be programmed to continuously compare the brain activity data to the control data during the procedure. That is, referring to FIG. 8, the processor 20 may create a control data model from the control data. During the procedure, the processor 20 may create a brain activity data model from the brain activity data. The processor 20 may then subtract the activity data model from the control model to obtain a comparison model. The system 10 may indicate that the subject is in pain if the peak of the comparison model is below a certain threshold, if the comparison model is shorter than a certain duration, or the like.

As yet another alternative, the processor 20 may be programmed to continuously perform statistical comparisons between the brain activity data and the control data during the procedure. For example, the processor 20 could create best-fit models for normal control data and innocuous control data obtained from the electronic server described above. Any portions of activity data significantly differing from the best-fit models could be considered noxious activity data. Other methods for determining substantial similarity between the activity data and the control data are described in the following example. Furthermore, various other methods for automatically comparing the activity data and the control data will be recognized by those skilled in the art and may be used without departing from the scope of the invention.

Figure 9:
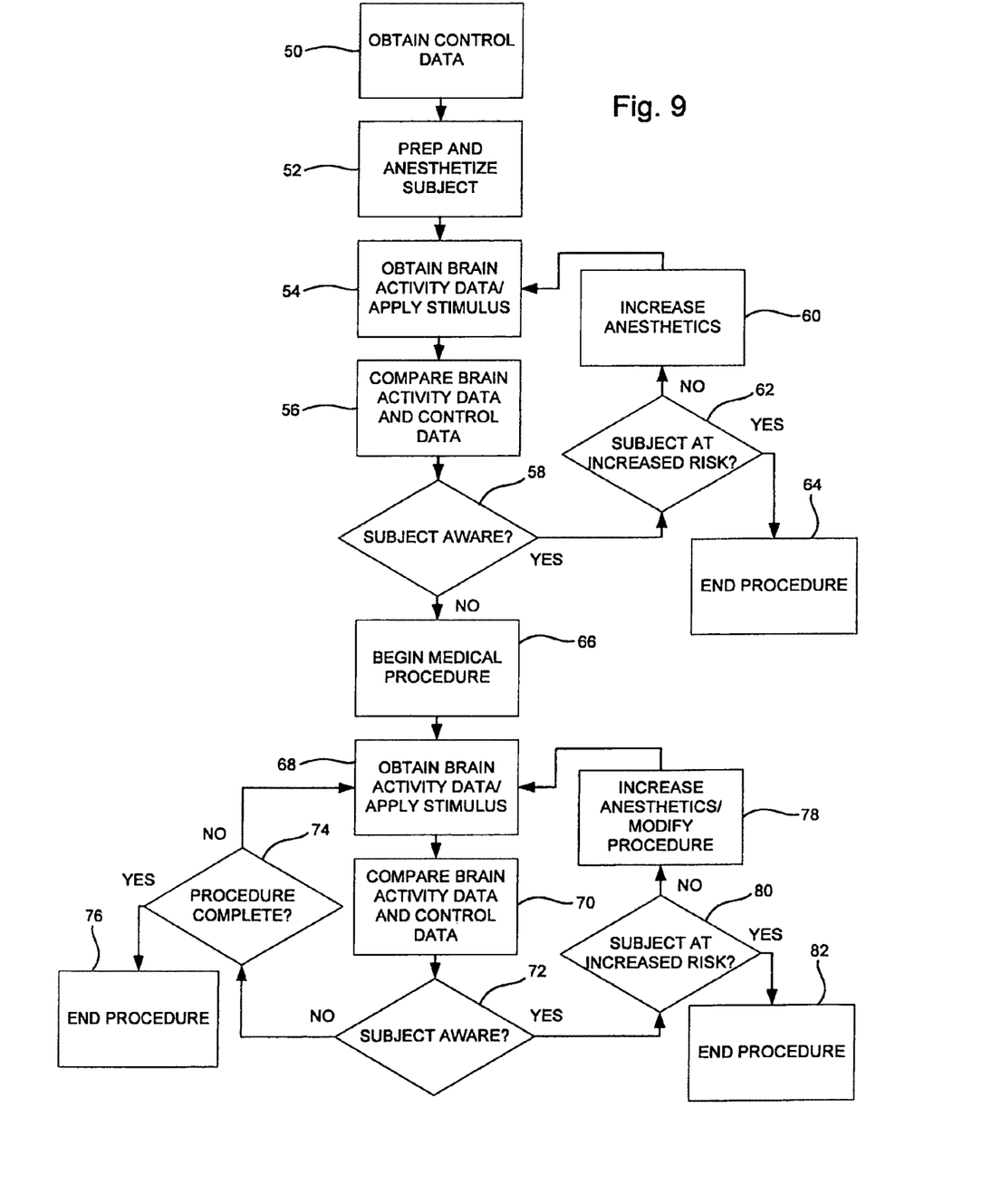
FIG. 9 is a flowchart of a method for monitoring an anesthetized patient for unintended awareness according to the present invention.

Referring now to FIG. 9, a method for monitoring an anesthetized patient for unintended awareness is summarized as follows. At step 50, control data corresponding to motion planning and/or sensations of pain are obtained. Noxious control data may be obtained by applying heat to the subject (e.g., via a thermode). Next, the subject is prepared for the medical procedure and anesthetized in a conventional manner at step 52. At step 54, the imaging system obtains brain activity data from the subject and, optionally, the same noxious stimulus (e.g., the thermode) is applied to the subject. The brain activity data are compared to the control data at step 56 to determine if the subject is aware at decision block 58. If the subject is aware, the medical practitioners may administer additional anesthetics to the subject at step 60. However, the practitioners may terminate the procedure if additional anesthetics would increase risk to the subject at decision block 62 and step 64. Returning to decision block 58, if the subject is not aware, the medical procedure (e.g., surgery) begins at step 66. At step 68, the imaging system again obtains brain activity data from the subject and, optionally, the same noxious stimulus is applied to the subject. The brain activity data are compared to the control data at step 70 to determine if the subject is aware at decision block 72. The result of this determination may be to provide an indication, such as an auditory indicator, a visual indicator, or another type of report. If the subject is not aware, the process returns to step 68 unless the medical procedure is completed at decision block 74 and step 76. If the subject is aware, at step 78 the medical practitioners may administer additional anesthetics or modify the procedure if an action in the procedure caused pain. However, the practitioners may terminate the procedure if additional anesthetics and modifying the procedure increase risk to the subject at decision block 80 and step 82.

Of course, the above method may be modified without departing from the scope of the invention. For example, the method may be conducted without obtaining control data, and instead the activity data may be reviewed for dataforms correlated with pain as described above. As another example, instead of applying the noxious stimulus at steps 54 and 68, the imaging system may simply monitor the subject for pain caused by actions of the medical procedure itself. As another example, the noxious stimulus need not be applied at steps 54 and 68 during each cycle. That is, the noxious stimulus may be applied only every several minutes or a few times an hour to reduce the tasks of the medical practitioners. However, the imaging system may continue to monitor the brain activity of the patient when the noxious stimulus is not applied. Brain activity at such times could be indicative of pain caused by actions of the medical procedure itself.

As briefly described above, medical practitioners may compare activity data from the imaging system 10 to control data for other purposes. For example, a medical practitioner may use methods of the present invention to objectively determine if a conscious subject is in pain and needs additional medication. Such determinations could aid in weaning subjects from addictive analgesics or aid in increasing medication to alleviate pain in non-communicative subjects (e.g., infants).

Figure 10:
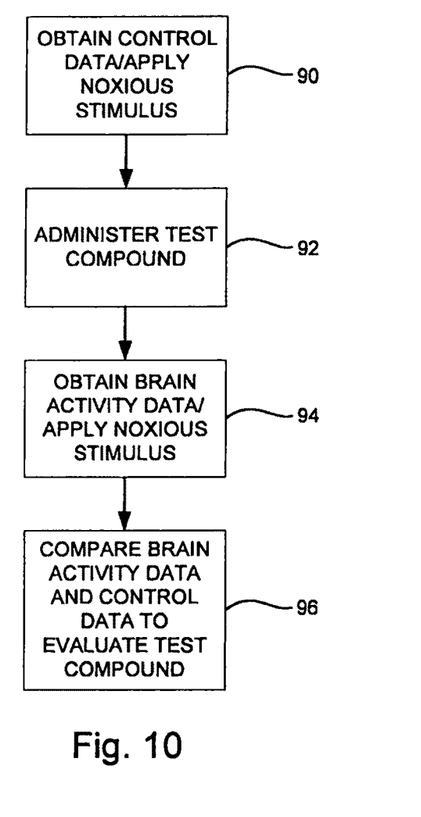
FIG. 10 is a flowchart of a method for evaluating therapeutic properties of a test compound according to the present invention.

As another example and referring now to FIG. 10, methods of the present invention may be used to identify potential analgesic compounds. Such a procedure is preferably as follows. At step 90, control data are obtained using the imaging system while subjecting a subject to a noxious stimulus. A test compound (i.e., a potential analgesic compound) is then administered to the subject at step 92. At step 94, brain activity data are obtained using the imaging system while again subjecting the subject to the noxious stimulus. The activity data are then compared to the control data at step 96 to determine if the subject experienced less pain after receiving the test compound (e.g., as indicated by a less intense change in blood flow rate or a shorter duration of intense blood flow from the activity data to the control data). Of course, the test compound is an analgesic if the subject experienced less pain after receiving the test compound.

Any compound may be employed in the method described above. For example, the method may be used to evaluate the analgesic properties of organic compounds, inorganic compounds, peptides or proteins, and nucleic acids (e.g., gene products). In addition, the method may also be used to evaluate non-chemical pain treatments, such as physical stimulation (e.g., via massage or acupuncture), heat stimulation, or electrical stimulation. The method may also be used to determine the length of time that a particular dose of a compound, or procedure, is effective by periodically monitoring brain activity data as a function of time.

Figure 11:
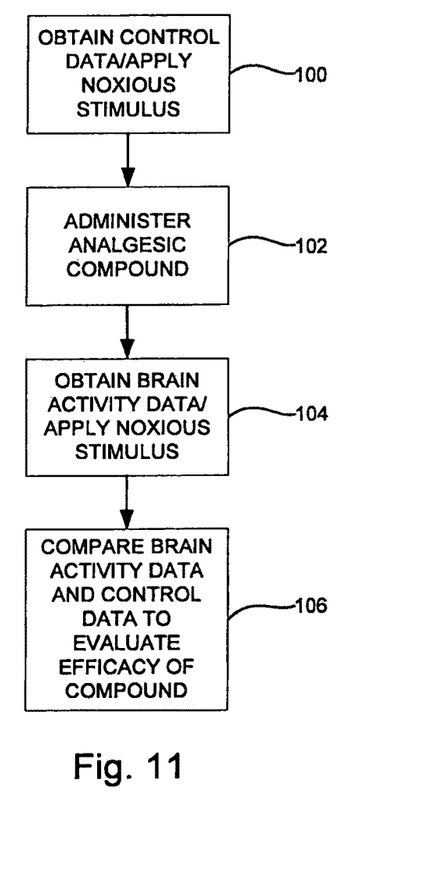
FIG. 11 is a flowchart of a method for evaluating the efficacy of an analgesic compound according to the present invention.

Similarly and referring now to FIG. 11, methods of the present invention may be used to evaluate the effectiveness of analgesic compounds and/or possible synergistic effects with other compounds. Such a procedure is preferably as follows. At step 100, control data are obtained using the imaging system while subjecting a subject to a noxious stimulus. An analgesic compound is then administered to the subject at step 102. At step 104, brain activity data are obtained using the imaging system while again subjecting the subject to the noxious stimulus. The activity data are then compared to the control data at step 106 to determine the extent to which the subject's pain was reduced (e.g., as indicated by differences in intensity of blood flow rate or differences in duration of intense blood flow rate from the activity data to the control data). As stated above, such methods may also be used with any non-chemical pain treatment.

Various similar methods may also be performed. For example, the imaging system may be used to obtain control data for a specific pain type (e.g., neuropathic, inflammatory, or acute) experienced by a subject. Such control data may subsequently be used to evaluate other subjects and determine courses of treatment.

EXAMPLE

Methods

Subjects

Nine healthy volunteers were recruited through local advertisements; all were right-handed males of 18-10 years in age. Subjects with a history of neurological trauma, neurological or psychiatric disorders, or diabetes were excluded. Subjects were also excluded if they were taking any psychoactive medications or were unable to keep their head still for a period of 360 consecutive seconds.

Equipment

The equipment has been described in detail elsewhere (Franceschini, M. A. et al., 2006. J. Biomed. Opt. 11, 054007). Briefly, a multichannel continuous-wave optical imager (CW5, TechEn Inc., Milford, Mass.) was used to emit the two wavelengths of light, 690 nm and 830 nm. These two wavelengths are used to measure changes in cortical deoxyhemoglobin (HbR) and oxyhemoglobin (HbO) concentration via differential absorption characteristics of the two wavelengths of light by these two molecules. The head probe used in this study consisted of 26 sources and 26 detectors (FIG. 2). Source fibers emitting the 690-nm wavelength were paired-off with those emitting the 830-nm wavelength to form an "optode." The main probe was arranged with one central, anterior-posterior row of 6-optodes per hemisphere. Each row of optodes was flanked on either side by a row of 6 detectors strategically placed 3 cm away from the sources in order to measure activation at cortical depth. Additionally, 2 optodes were placed on the forehead in order obtain prefrontal cortex activation. These two source optodes were similarly flanked on either side by single detectors. During the experiment, subjects were connected to a physiological monitor for continuous monitoring of heart rate (pulse oximeter; Norin Medical Inc., Plymouth, Minn.), respiratory rate (strain gauge belt; Sleepmate/Newlife Technologies, Resp-EZ, Midlothian, Va.), and blood pressure (in-house, custom-made device). Subjects remained sitting in a reclined position for the duration of the experiment. Lights were turned off in the room during data acquisition to minimize signal contamination from ambient light sources.

Paradigm

Tactile (brush) stimuli were delivered manually to each subject's hand using a soft toothbrush. Prior to the experiment a 3×3 $cm^2$ area of the dorsum of the right hand was marked for stimulus (brush or heat) delivery. Care was taken to consistently deliver the stimulus to the same location on the hand and to apply the same amount of pressure each time. The same investigator applied the stimuli to all subjects. A 3×3 $cm^2$ thermode (TSA-2001, Medoc Inc., Haifa, Israel) was used to deliver the painful 46° C. thermal stimuli. This equipment has been used in other fMRI pain experiments (Becerra, L. et al., 2001. Neuron 32, 927-946). The thermal probe was lowered down onto the hand of the subject upon prompting and removed at the end of each stimulus. The probe was always applied with a similar force (pressure) predetermined at the beginning of the experiment with a scale to be around 2 lb. For both brush and heat, the paradigm consisted of 26 stimuli of 5-s duration over 6 minutes with a jittered inter-stimulus interval (ISI) of 6-13 s and average IS1 of 8.5 s. The paradigm was applied twice for each stimulus type. Prompts to apply stimuli were presented audibly via headphones to the investigator. Subjects were asked at the end of the thermal scan to rate the pain intensity of the stimuli in a Likert 11-point scale (0, no pain, 10, maximum pain).

Data Analysis

Analysis was carried out using the open source software Homer which is implemented in Matlab (Mathworks, Natick, Mass.). The analysis has been described in detail elsewhere Franceschini, M. A. et al., 2006. J. Biomed. Opt. 11, 054007). Here, data was corrected for motion artifacts using principal component analysis in a similar manner to the procedure previously outlined elsewhere Wilcox, T. et al., 2005. Biomed Opt. 10, 11010). Single trial averages (STAs) were calculated for each detector for the oxy-(HbO) and deoxyhemoglobin (HbR) changes detected. The resulting data were displayed spatially for each detector and the signal corresponding to the somatosensory cortex was identified on the contralateral hemisphere to the stimulated side. The farthest posterior response used was the Source 5-Detector 5 pairing, and the farthest anterior response taken was the Source 3-Detector 3 pairing. For simplicity, this activation is referred in this example as S1 activation. The signal corresponding to ipsilateral S1 was identified as the mirroring ipsilateral source-detector pairings corresponding to those considered to be S1 on the contralateral side.

Hemodynamic Model Decomposition and Group Statistical Analysis

Average HbO STA for brush and heat in S1 depicted potentially monophasic (brush) and biphasic (heat) responses, respectively (FIG. 3). Individual responses to brush and heat were fitted nonlinearly using a one or two gamma response model, respectively. Gamma functions included a delay factor (tau) as presented in the following equation:

$$H(t-\tau) = (t-\tau)^{a} * \exp(-(t-\tau)*b)$$

The non-linear fit was carried out using Matlab. The fit parameters were used to calculate time to peak (TTP) for brush and heat responses:

$$TTP = \tau + a/b$$

Group statistics were obtained by the following approach: For brush, individual HbO changes to the 26 stimuli were fitted linearly with an explanatory variable (EV) constructed from the temporal profile of the stimuli convoluted with a standard hemodynamic response (gamma function With delay of 6 s and standard deviation of 3 s; see Becerra, L. et al., 2001. Neuron 32, 927-946). For heat, following our previous fMRI study, two EVs were used (one delayed 10 s from the other; see Becerra, L. et al., 2001. Neuron 32, 927-946). Parameter estimates (PE) and residual variances for each EV were carried out to perform group level analysis. Group results were obtained using a fixed effects approach as described elsewhere (Beckmann, C. F. et al., 2003. Neurohage 20, 1052-1063); briefly, to calculate the group average each individual parameter estimate is weighted by the inverse of the residual variance (hence, subjects with large variances might have their contribution attenuated even if they have large PEs). For group activation comparisons (i.e., contralateral vs. ipsilateral), a pair-wise approach was used. A corrected p value (0.05126 detectors=0.002) was used as threshold for statistical significance.

Results

Subjects

Nine subjects were recruited to the study. All nine data sets for the brush stimuli were kept, while one data set for the thermal stimuli was eliminated due to an excessive number of motion artifacts. Subjects with data included in the results were 29±6 years of age.

Pain Scores

None of the subjects perceived brush stimulation as painful (average rating 1.6±1.0). Subjects rated the painful stimuli as 5.0±2.1 that is considered moderately painful. None of the subjects prematurely terminated the experiment because of excessive pain.

Brush Stimulation

FIG. 3 depicts average S1 group activation to brush as detected in the HbO signal contralateral (line 30) and ipsilateral (line 32) to the stimulus. In addition, the HbR signal is depicted in the same figure (contralateral-line 31, ipsilateral-line 33). Average group activation in frontal areas is displayed in FIG. 4. The group activation was statistically significant ($p<0.002$) for both contralateral and ipsilateral activation in S1 and frontal areas. Comparing the contralateral response vs. the ipsilateral one, the difference was significant for S1 ($P<0.002$) but not for frontal areas ($p=0.06$). For both frontal and S1 areas, brush stimulation elucidated a single hemodynamic response.

Heat Stimulation

Noxious stimulus elicited moderately painful sensations. S1 activation was observed bilaterally to the same level of activation, a similar result obtained with other neuroimaging techniques (Hansson, T. et al., 1999. Neurosci: Lett 271, 29-32). It is important to note that systemic effects were ruled out for each subject through the use of a head probe that maps a large area of the cortex. Responses used for averaging were localized to their respective ROIs and did not occur ubiquitously across all of the detectors.

Activations in S1 (FIG. 3) as detected in the HbO signal contralateral (line 34) and ipsilateral (line 36) are very similar in size and temporal profile. Both responses seem to display two waves or phases (early and late). Frontal activation was different in its temporal profile (FIG. 4) with an initial contralateral negative change in HbO. Group results indicated significant contralateral and ipsilateral activation ($p<0.002$) in S1 and only late phase in the frontal areas (ipsilateral: $p<0.002$). Comparing contralateral vs. ipsilateral activation, the difference was found not significant in S1 and frontal areas ($p=0.16$).

Time to Peak

Non-linear fit results for one response for brush and two responses for heat are displayed in FIG. 6. The TTP for brush and the first (early) heat response were 6.42±0.50 and 5.49±0.68 s, respectively, and were not significantly different from each other. The second (late) response to heat had a TTP of 12.60±0.83 and it was significantly different from brush or the early heat response.

Discussion

Our results indicate a robust signal in somatosensory cortex to mechanical and painful stimuli can be measured. However, the temporal and spatial characteristics of the hemodynamic responses to these two stimuli are markedly different from each other. Furthermore, a positive change in frontal areas to brush stimuli but an early negative change to heat stimuli was also observed. Collectively, these results might indicate that it is possible to discern differences in the pattern of activation between painful and non-painful stimuli based on the spatial and temporal characteristics using DOI.

Our results, point to a robust activation to a pure dynamic mechanical stimulation with no noxious component on both hemispheres with a larger response contralateral to the stimulated side. These results seem to validate studies employing electrical stimulation as non-painful sensory with a significant contralateral activation and a weaker ipsilateral response.

As depicted in FIG. 3, the hemodynamic response to heat is double-peaked compared to the brush response. The early peak in the heat response resembles the brush response. In this example, a significant activation in the frontal regions of the brain was observed. Activation in this example was bilateral to brush and predominantly ipsilateral to the pain stimulus.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

We claim:

1. A method for recognizing conscious or unconscious pain sensation in a subject comprising the steps of:
   a) acquiring, using an optical imaging system, optical imaging data from at least one cortical region of the brain of the subject over a time period;

b) measuring, using the optical imaging data, at least one hemodynamic parameter in the at least one cortical region of the brain of the subject;
c) identifying a variation pattern in the measured hemodynamic parameters;
d) comparing the variation pattern to at least one predetermined variation pattern associated with subject conscious or unconscious pain sensation to determine a substantial similarity between the variation pattern and the predetermined variation pattern;
e) providing an indication of conscious or unconscious pain sensation of the subject;
f) changing a dose of anesthetics or modifying a procedure based on the indication of conscious or unconscious pain sensation of the subject; and
g) after said changing a dose of anesthetics or said modifying a procedure based on the indication of conscious or unconscious pain sensation of the subject, repeating steps a) through e).

2. The method of claim 1, wherein the hemodynamic parameter is blood flow.

3. The method of claim 2, wherein step b) includes detecting optical signals from oxygenated hemoglobin to measure blood flow.

4. The method of claim 1, wherein the at least one cortical region of the brain is selected from the somatosensory cortex, the supplementary motor cortex, and the frontal cortex.

5. The method of claim 1, wherein the hemodynamic parameter is blood flow and additionally comprising the step of performing an activity on the subject configured to inflict pain on the subject.

6. The method of claim 5, wherein the predetermined variation pattern indicating conscious or unconscious pain sensation comprises two sequential peaks in blood flow over time, the two sequential peaks signaling a sensation of pain in the subject.

7. The method of claim 6, wherein step a) includes acquiring the optical imaging data bilaterally on the somatosensory cortex, and wherein the predetermined variation pattern associated with conscious or unconscious pain sensation bilaterally comprises two sequential peaks in blood flow over time.

8. The method of claim 5, wherein step d) includes determining whether a time delay between performing the activity and an occurrence of a peak in blood flow is indicative of a sensation of pain in the subject.

9. The method of claim 8, wherein determining a time delay of greater than about ten seconds is determined to be indicative of a sensation of pain in the subject.

10. The method of claim 5, additionally comprising the step of applying an innocuous test stimulus to the subject.

11. The method of claim 10, wherein step a) includes acquiring the optical imaging data bilaterally on the somatosensory cortex, and wherein the predetermined variation pattern indicating conscious or unconscious pain sensation contains both ipsilateral and contralateral optical imaging data.

12. The method of claim 11, wherein the predetermined variation pattern associated with conscious or unconscious pain sensation comprises a substantially reduced peak of blood flow with respect to time in the ipsilateral somatosensory cortex as compared to the contralateral somatosensory cortex, the reduced peak signaling a sensation of innocuous touch in the subject.

13. The method of claim 12, wherein the predetermined variation pattern shows peak blood flow with respect to time in the ipsilateral somatosensory cortex is approximately 55 percent of the peak blood flow with respect to time in the contralateral somatosensory cortex.

14. The method of claim 1, wherein the at least one predetermined variation pattern associated with conscious or unconscious pain sensation is obtained from control data for the hemodynamic parameter.

15. The method of claim 14, wherein the control data is obtained by the additional step of acquiring the optical imaging data from the at least one cortical region of the subject's brain when the subject is conscious.

16. The method of claim 15, further comprising the step of administering an anesthetic to the subject after obtaining the control data.

17. The method of claim 1, wherein the blood flow pattern comprises a rounded peak of maximum blood flow.

18. The method of claim 1 wherein the optical imaging system is a diffuse optical imaging system.

19. The method of claim 1 wherein the optical imaging system is a near infrared spectroscopy (NIRS) system.

* * * * *

UNITED STATES PATENT AND TRADEMARK OFFICE
CERTIFICATE OF CORRECTION

PATENT NO. : 8,951,202 B2  Page 1 of 1
APPLICATION NO. : 12/658897
DATED : February 10, 2015
INVENTOR(S) : David Borsook et al.

It is certified that error appears in the above-identified patent and that said Letters Patent is hereby corrected as shown below:

In The Claims

Column 5, line 10  -  "3" should be --β--

Signed and Sealed this
Second Day of June, 2015

Michelle K. Lee
*Director of the United States Patent and Trademark Office*